(12) United States Patent
Mayer

(10) Patent No.: US 7,921,625 B1
(45) Date of Patent: Apr. 12, 2011

(54) METHOD FOR IMPERMANENT SEALED PERFORATION OF THIN-WALLED PACKAGING

(75) Inventor: Daniel W. Mayer, Wyoming, MN (US)

(73) Assignee: Mocon, Inc., Minneapolis, MN (US)

( * ) Notice: Subject to any disclaimer, the term of this patent is extended or adjusted under 35 U.S.C. 154(b) by 1797 days.

(21) Appl. No.: 11/077,912

(22) Filed: Mar. 11, 2005

(51) Int. Cl.
*B65B 31/08* (2006.01)

(52) U.S. Cl. ............................... 53/434; 53/512; 73/49.3

(58) Field of Classification Search .................... 53/432, 53/434, 510, 512; 73/49.3; *B65B 31/08*
See application file for complete search history.

(56) References Cited

U.S. PATENT DOCUMENTS

| | | | |
|---|---|---|---|
| 2,749,744 A * | 6/1956 | Doudera, Jr. et al. | 73/52 |
| 3,496,969 A * | 2/1970 | Bruce et al. | 141/20 |
| 4,133,736 A * | 1/1979 | Nakagawa et al. | 204/409 |
| 4,733,555 A * | 3/1988 | Franks | 73/49.3 |
| 4,919,955 A * | 4/1990 | Mitchell | 53/432 |
| 5,066,279 A | 11/1991 | Russell | |
| 5,099,679 A * | 3/1992 | Huerlimann et al. | 73/19.06 |
| 5,212,993 A * | 5/1993 | Mayer | 73/864.21 |
| 5,347,845 A * | 9/1994 | Kepler | 73/31.03 |
| 5,481,852 A * | 1/1996 | Mitchell | 53/432 |
| 5,531,672 A | 7/1996 | Lynn | |
| 5,562,639 A | 10/1996 | Lynn et al. | |
| 6,070,397 A * | 6/2000 | Bachhuber | 53/512 |
| 6,155,027 A * | 12/2000 | Brooks | 53/434 |
| 2004/0126279 A1 | 7/2004 | Renzi et al. | |

FOREIGN PATENT DOCUMENTS

| | | |
|---|---|---|
| JP | 5-253299 | 10/1993 |
| WO | WO 95/35126 A1 | 12/1995 |
| WO | WO 96/09539 A1 | 3/1996 |
| WO | WO 02/36182 A2 | 5/2002 |

\* cited by examiner

*Primary Examiner* — Stephen F Gerrity
(74) *Attorney, Agent, or Firm* — Sherrill Law Office, PLLC

(57) ABSTRACT

An instrument for impermanent sealed perforation of thin-walled, hermetically sealed packaging. The instrument includes a longitudinally tapered needle and a septum with a hole. The underside of the septum is coated with a pressure sensitive adhesive. The hole through the septum is configured and arranged to permit unrestricted passage of the distal longitudinal end portion of the needle through the hole, while sealingly engaging the longitudinal midsection of the needle. The septum is incapable of sealing the hole through the septum after withdrawal of the needle from the hole.

10 Claims, 3 Drawing Sheets

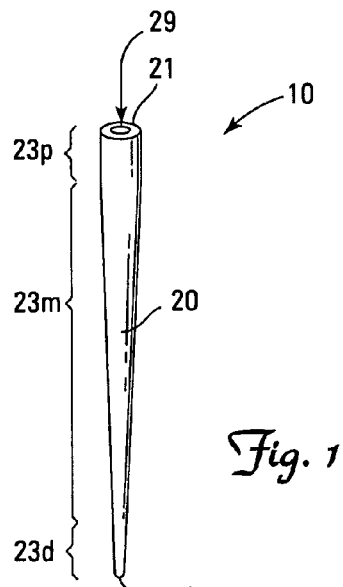
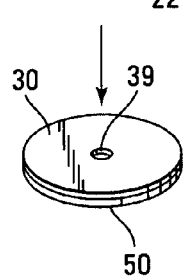
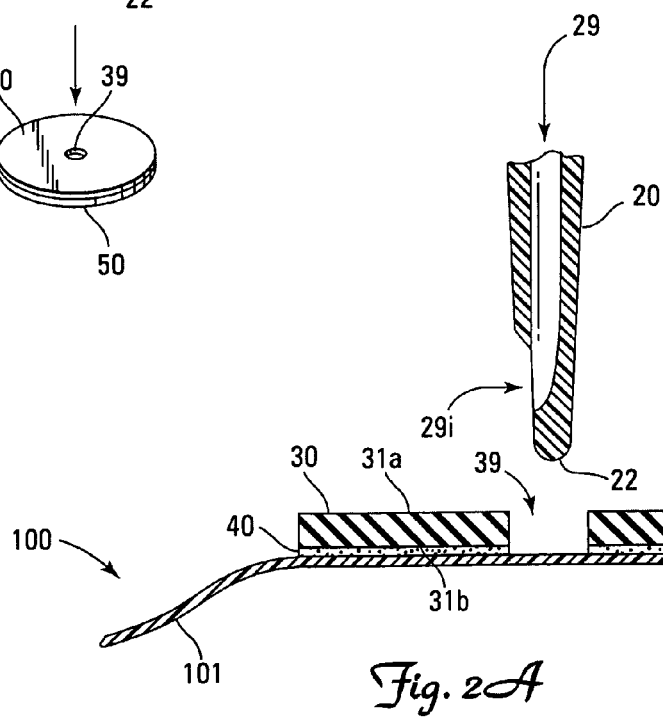
Fig. 1
Fig. 2A

METHOD FOR IMPERMANENT SEALED PERFORATION OF THIN-WALLED PACKAGING

FIELD OF INVENTION

The invention relates to instruments and techniques for sealed perforation of hermetically sealed packaging in order to withdraw unadulterated gaseous content from the packaging.

BACKGROUND

Products susceptible to spoilage, such as processed foods, nuts and sliced fruits and vegetables, are often placed in hermetically sealed packaging which has been flushed with an inert gas, such as nitrogen or argon, to achieve an oxygen concentration within the packaging of less than about 3% and thereby prolong the shelf-life of the product. Such packaging is commonly known as controlled atmosphere packaging (CAP) or modified atmosphere packaging (MAP).

Insufficient flushing and leaks in the packaging can significantly reduce the anticipated shelf life, resulting in undesired spoilage. Hence, production involving CAP/MAP typically includes periodic testing of the gaseous content of the packaging to measure the oxygen level in the packaging and/or detect the presence of any leaks in the packaging in an effort to guide changes or adjustments in the production process (e.g., increase or decrease the flow of $N_2$ into the fill and seal area of the packaging process) and/or aid in determining the shelf-life of the packaged product and thereby aid the production facility in selecting product for shipment in order to reduce spoilage (e.g., shipping product from inventory based upon shortest remaining estimated shelf life).

A variety of instruments and methods are known for withdrawing gaseous samples from CAP/MAP, most of which involve sealed perforation of the packaging with a hollow needle. In order to prevent the tester from accidentally sticking themselves with the needle during the testing procedure, the devices commonly employ some type of a safety system which prevents the tester from directly accessing the needle (e.g., packaging to be tested must be placed within an enclosed chamber with the access door closed before the needle can be extended from within a protective sheathing towards the packaging). While effective for preventing accidental sticking of the tester, such systems are expensive, cumbersome to operate and difficult to transport.

Accordingly, a substantial need exists for an inexpensive and portable instrument which can quickly, easily and safely perforate packaging for purposes of withdrawing unadulterated gaseous content from the packaging.

SUMMARY OF THE INVENTION

A first aspect of the invention is an instrument for impermanent sealed perforation of a thin-walled, hermetically sealed packaging. The instrument includes a needle and a septum. The needle is a longitudinally-tapered, blunt-tipped, needle having a longitudinal lumen, a proximal longitudinal end portion, a distal longitudinal end portion and a longitudinal midsection. The septum has a pressure sensitive adhesive coating on an underside of the septum, and a hole. The hole through the septum is configured and arranged to permit unrestricted passage of the distal longitudinal end portion of the tapered needle through the hole, and sealingly engage the longitudinal midsection of the tapered needle. The septum is incapable of sealing the hole through the septum after withdrawal of the tapered needle from the hole.

A second aspect of the invention is a method for impermanent sealed perforation of a thin-walled, hermetically sealed packaging. The method involves the steps of (i) obtaining a septum having a hole, (ii) obtaining a longitudinally-tapered, blunt-tipped, needle having a longitudinal lumen, a proximal longitudinal end portion, a distal longitudinal end portion and a longitudinal midsection, (iii) adhering the septum to a packaging wall, (iv) inserting the distal longitudinal end portion of the needle through the hole in the septum until the needle perforates the packaging wall so as to form an opening through the wall, and the longitudinal midsection of the tapered needle is sealingly wedged within the hole, (v) removing content from the packaging through the lumen, and (vi) withdrawing the needle from the hole in the septum. Withdrawal of the needle from the hole in the septum leaves an unsealed hole through the septum and an unsealed opening through the packaging wall.

BRIEF DESCRIPTION OF THE DRAWINGS

FIG. 1 is a perspective view of one embodiment of the invention.

FIG. 2A is an enlarged cross-sectional side view of the invention shown in FIG. 1 with the septum adhered to the sidewall of packaging.

DETAILED DESCRIPTION OF THE INVENTION INCLUDING A BEST MODE

Nomenclature

Figure 2B:
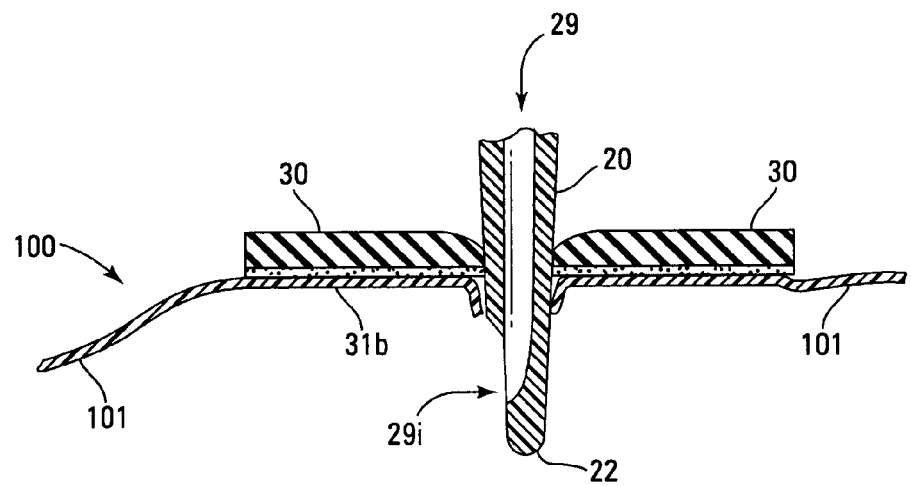
FIG. 2B is an enlarged cross-sectional side view of the invention shown in FIG. 2A with the needle sealingly wedged within the hole through the septum.

| | |
|---|---|
| 10 | Instrument |
| 20 | Needle |
| 21 | Proximal End of Needle |
| 22 | Distal End or Tip of Needle |
| 23d | Distal End Portion of Needle |
| 23m | Midsection of Needle |
| 23p | Proximal End Portion of Needle |
| 29 | Lumen through Needle |
| 29i | Lumen Access Opening through Tip of Needle |
| 30 | Septum |
| 31a | Upper Major Surface or Topside of Septum |
| 31b | Lower Major Surface or Underside of Septum |
| 39 | Hole through Septum |
| 40 | Pressure Sensitive Adhesive Coating |
| 50 | Release Liner |
| 100 | Packaging |
| 101 | Sidewall of Packaging |

Definitions

As utilized herein, including the claims, the phrase "blunt-tipped" means a tip sharp enough to penetrate thin-walled Mylar™ packaging with modest hand-applied force but insufficient to penetrate human skin with modest hand-applied force whereby a "blunt-tipped" needle remains effective for use in perforating thin-walled packaging while preventing accidental penetration through human skin during normal use of the needle.

As utilized herein, including the claims, the phrase "thin-walled" means a wall having a thickness of less than about 0.1 mm.

Construction

As shown in FIG. 1, a first aspect of the invention is an instrument 10 for sealed perforation of hermetically sealed packaging 100 in order to withdraw unadulterated gaseous content (not shown) from the packaging 100

The instrument 10 can be effectively employed with a wide variety of thin-walled hermetically sealed packaging 100 ranging from fairly rigid packaging 100 such as thin-walled polyvinyl chloride tubes, through semi-flexible packaging 100 such as wax-coated cartons and thin-walled polyethylene bottles, to flexible packaging such as bags made from polyethylene terephthalate (i.e., MYLAR®) or polyethylene films.

Referring to FIG. 1, the instrument 10 includes a needle 20 and a septum 30.

As shown in FIG. 1, the needle 20 is longitudinally tapered towards the distal end 22 of the needle 20 and defines a proximal end portion 23p, a distal end portion 23d, and a midsection 23m therebetween.

The needle 20 is configured and arranged with a longitudinal lumen 29. The proximal end portion 23p of the needle 20 shown in FIG. 1 is generically shown, but will typically be configured and arranged for sealed connection to flexible tubing (not shown).

Figure 3:
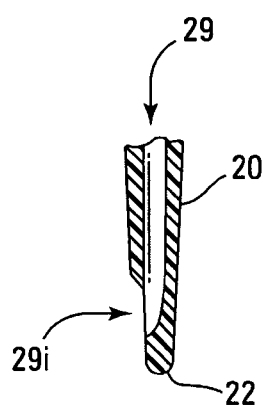
FIG. 3 is an enlarged cross-sectional side-view of one embodiment of the tip portion of a blunt-tipped needle.
Figure 4:
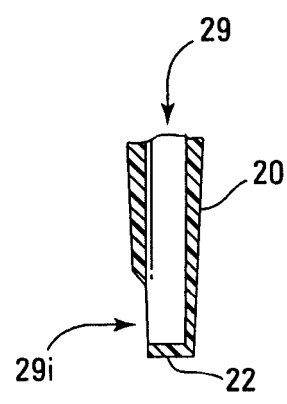
FIG. 4 is an enlarged cross-sectional side-view of a second embodiment of the tip portion of a blunt-tipped needle.
Figure 5:
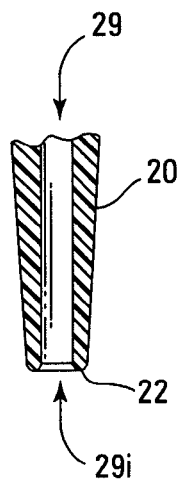
FIG. 5 is an enlarged cross-sectional side-view of a third embodiment of the tip portion of a blunt-tipped needle.

The distal end 22 of the needle 20 is blunt—meaning the tip 22 is sharp enough to penetrate thin-walled Mylar™ packaging 100 with modest hand-applied force but insufficient to penetrate human skin with modest hand-applied force. The tip 22 of the needle 20 can be blunted by any of the common techniques including rounding of the tip 22 as shown in FIG. 3 or flattening of the tip 22 as shown in FIGS. 4 and 5. The dimensions of the tip 22 necessary to provide a blunt tip 22 depend upon a number of factors including the material of construction (e.g., flexible plastic v. metal) and the shape of the tip 22 (e.g., rounded v. flat). Generally, a blunt tip can be achieve by providing a rounded tip 22 with a radius of about 0.2 to 0.7 mm or providing a flat tip 22 with a radius of about 0.1 to 0.6 mm. A radius of less than the suggested minimum can penetrate human skin under a modest hand-applied force (e.g. accidental sticks are possible) while a radius of greater than the suggested maximum requires excessive force to penetrate the sidewall 101 of typical thin-walled packaging 100.

The needle 20 can be configured and arranged with a side access port 29i as shown in FIGS. 3 and 4 or an end access port 29i as shown in FIG. 5, with a preference for a side access port 29i in order to reduce the chances of plugging the access port 29i with a piece of the packaging 100 during perforation of the packaging 100.

The needle 20 may be constructed from any of the materials commonly used in the manufacture of needles including specifically, but not exclusively, metals such as stainless steel and plastics such as polypropylene.

Referring to FIGS. 1 and 2A-2C, the septum 30 has a hole 39 therethrough configured and arranged to accommodate introduction and unrestricted passage of the distal end 22 of the needle 20 through the hole 39 while permitting the septum 30 to sealingly engage the midsection 23m of the needle. The septum 30 is intended to be used as a disposable item and is preferably a single thin layer of an inexpensive material having a simple flat profile.

The underside 31b of the septum 30 is coated with a pressure sensitive adhesive 40 so that the septum 30 may be sealingly applied to the sidewall 101 of packaging 100. A release liner 50 is provided over the pressure sensitive adhesive 40. The septum 30 serves to both sealingly engage an inserted needle 20, and prevent creation of an elongated rip in the sidewall 101 of the packaging 100 when perforating the sidewall 101 with the needle 20.

The septum 30 may be constructed from any of the materials commonly used in the manufacture of septums including specifically, but not exclusively, flexible plastics such as polyethylene and polypropylene, and natural and synthetic rubbers.

The radius of the distal end 22 of the needle 20, the angle of taper of the needle 20 and the radius of the hole 39 through the septum 30 need to be cooperatively selected so that a user may easily and consistently introduce the distal end 22 of the needle 20 into the hole 39 by hand (e.g., tip radius substantially smaller than hole radius), and the midsection 23m of the needle 20 will sealingly engage the septum 30 after insertion of the needle 20 through the hole 39 a distance sufficient to ensure that the access opening 29i in the tip 22 of the needle 20 is positioned entirely within the confines of the packaging 100.

Use

Figure 2C:
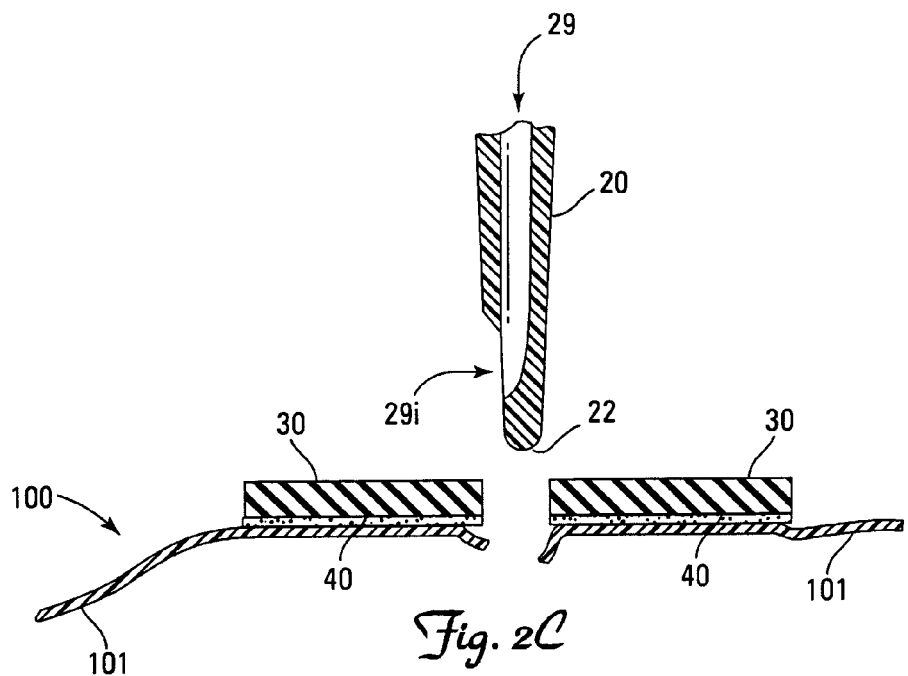
FIG. 2C is an enlarged cross-sectional side view of the invention shown in FIG. 2A with the needle withdrawn from the hole through the septum.

Referring generally to FIGS. 2A-2C, the instrument 10 is used by (i) peeling the release liner 50 from the underside of the septum 30 to reveal the pressure sensitive adhesive 40, (ii) adhering the septum 30 to a sidewall 101 of packaging 100 to be tested, (iii) introducing the tip 22 of the needle 20 into the hole 39 in the septum 30, and (iv) inserting the needle 20 through the hole 39 a sufficient distance and under sufficient force to perforate the sidewall 101 of the packaging 100 and sealing wedge the midsection 23m of the needle 20 within the hole 39. When testing of the contents of the perforated packaging 100 is complete, the needle 20 may simply be withdrawn and the perforated packaging 100 discarded along with the attached septum 30. The procedure may then be repeated for another packaging 100 using the same needle 20 and a new septum 30.

The instrument 10 is particularly suited and adapted for use in removing unadulterated gaseous content from hermetically sealed CAP/MAP packaging 100.

I claim:

1. A method for impermanent sealed perforation of a thin-walled, hermetically sealed packaging, comprising:
   (a) obtaining a septum having a hole,
   (b) obtaining a longitudinally-tapered, blunt-tipped, needle having a longitudinal lumen, a proximal longitudinal end portion, a distal longitudinal end portion and a longitudinal midsection,
   (c) adhering the septum to a wall of the packaging,
   (d) inserting the distal longitudinal end portion of the needle through the hole in the septum until the needle perforates the wall of the packaging so as to form an opening through the wall, and the longitudinal midsection of the tapered needle is sealingly wedged within the hole,
   (e) removing content from the packaging through the lumen,
   (f) withdrawing the needle from the hole in the septum so as to leave an unsealed hole through the septum and an unsealed opening through the wall of the packaging.

2. The method of claim 1 wherein the lumen has an access port through a sidewall of the distal end portion of the needle.

3. The method of claim 1 wherein the tip is (i) flat with a radius of about 0.1 to 0.6 mm or (ii) rounded with a radius of about 0.2 to 0.7 mm.

4. The method of claim 1 wherein the needle is plastic.

5. The method of claim 1 wherein the septum is a rubber septum.

6. The method of claim 1 wherein the septum is flat and thin.

7. The method of claim 1 wherein the packaging is controlled atmosphere packaging.

8. The method of claim 7 wherein the step of removing content from the packaging comprises removing gaseous content from the packaging.

9. The method of claim 8 further comprising the step of repeating steps (a)-(f) using the same needle and a different septum on another packaging.

10. The method of claim 1 further comprising the step of repeating steps (a)-(f) using the same needle and a different septum on another packaging.

* * * * *